United States Patent [19]

Komurasaki et al.

[11] Patent Number: 5,847,084
[45] Date of Patent: Dec. 8, 1998

[54] PROCESS FOR OBTAINING PLATELET FACTOR-4

[75] Inventors: Yoshikazu Komurasaki, Miki; Chihiro Shindoh, Kobe; Takashi Hirose, Kobe; Keihide Koh, Kobe; Satoshi Nishimuro, Kobe, all of Japan

[73] Assignee: JCR Pharmaceuticals Co., Ltd., Hyogo, Japan

[21] Appl. No.: 749,401

[22] Filed: Nov. 15, 1996

[30] Foreign Application Priority Data

Nov. 17, 1995 [JP] Japan .................................. 7-324035

[51] Int. Cl.⁶ .......................... A61K 35/14; C08B 37/08; C08B 37/10

[52] U.S. Cl. .......................... 530/380; 530/395; 530/412; 530/415; 530/417; 536/20; 536/21

[58] Field of Search ..................................... 530/380, 415, 530/395, 412, 417; 502/404; 536/20, 21

[56] References Cited

U.S. PATENT DOCUMENTS

| | | | |
|---|---|---|---|
| 4,278,594 | 7/1981 | Amrani | 530/383 |
| 4,576,928 | 3/1986 | Tani et al. | 502/404 |
| 4,894,440 | 1/1990 | Rosenberg | 530/351 |
| 5,053,133 | 10/1991 | Klein et al. | 210/500.38 |
| 5,258,502 | 11/1993 | Kuranda | 530/350 |
| 5,298,488 | 3/1994 | Kojima et al. | 514/8 |
| 5,324,823 | 6/1994 | Asakawa et al. | 530/415 |
| 5,482,923 | 1/1996 | Maione | 514/2 |

FOREIGN PATENT DOCUMENTS

| | | |
|---|---|---|
| 0 260 918 A | 3/1988 | European Pat. Off. . |
| 0 589 719 A | 3/1994 | European Pat. Off. . |

OTHER PUBLICATIONS

Cook et al. Circulation. vol. 85 (3), pp. 1102–1109, 1992.
Beena et al. J. Biomat. Appl. vol. 8 (4), pp. 385–403, Abstract enclosed, 1994.
Chandy et al. Artificial Organs. vol. 16 (6), pp. 568–576, Abstract enclosed, 1992.
Genet. Eng. News. Aug. 1994, vol. 14 (14), p. 49, Abstract enclosed, 1994.
Myers, et al., "Expression And Purification Of Active Recombinant Platelet Factor 4 From A Cleavable Fusion Protein," XP000652643, vol. 2, 1991, pp. 136–143.

*Primary Examiner*—Leon B. Lankford, Jr.
*Assistant Examiner*—Christopher R. Tate
*Attorney, Agent, or Firm*—Jacobson, Price, Holman & Stern, PLLC

[57] ABSTRACT

The present invention, using a readily available sulfated chitin as an adsorbent, can permit platelet factor-4 to be recovered through specific adsorption from a solution containing the same factor, in by far increased yields as compared with the conventional process utilizing a heparin-immobilized affinity column, and provides the process for isolating, through purification platelet factor-4 which is suited for a commercial-scale, mass production process, wherein there can be offered the advantages of utilization of more readily available sulfated chitin, simplified procedure and improved production yields for the objective substance.

6 Claims, 2 Drawing Sheets

PROCESS FOR OBTAINING PLATELET FACTOR-4

The present invention relates to a process for producing through purification platelet factor-4.

BACKGROUND OF THE INVENTION

In the open intracardiac surgeries, such as cardiac bypass surgery, arrest or intervention of bloodstream into and out of the heart is necessary for a limited period of time, and a heart-lung machine is used to take over temporarily the functions of the heart and the lungs. In order to prevent blood coagulation within such heart-lung machine, heparin is loaded to the blood flowing therein, and after the surgical operations, protamine sulfate is administered to the patients to secure the recovery of their blood coagulation functions. In the blood dialysis therapy for patients with renal function failures, heparin and protamine sulfate are used for the similar purpose. Nevertheless, administration of protamine sulfate is known to cause a variety of side effects, such as allergic reaction, decreases in counts of platelets and white blood cells, hypotension, bradycardia, dyspnea, heat, transient rubeosis, nausea/vomiting and pulmonary edema, and adequate attention is therefore required to be exercised (Japanese Pharmacopoeia, the 12th revised edition; Viera, J., et al., J. O. Surgeon, 50, 151, 1984).

On the other hand, it was reported that a heparin-neutralizing substance is found to exist in platelets on the basis of found variabilities of platelet's heparin-neutralizing activity depending upon the magnitude of platelet counts (Conley, C. L., et al. Proc. Sol. Exp. Biol. Med., 69, 284–287, 1948). As a heparin-neutralizing substance in platelets, thereafter, reports were published that there exist not only platelet factor-4 (hereinafter referred to briefly as "PF4") but also β-thromboglobulin, low-affinity PF4, basic platelet protein, fibronectin, thrombospondin, etc., and it was discovered that PF4, among others, is the most potent affinity toward heparin. PF4 is a protein having a molecular weight of 7.8 kDa, and was reported to elaborate heparin-neutralizing activity without accompaniment of the side effects (leukopenia, hypotension, pulmonary edema) produced by protamine sulfate administered (Cook, J. J., et al., Circulation, 85, 3, 1992). Such being the case, PF4 is expected to act as a heparin-neutralizing agent which is a replacement for protamine sulfate.

In addition to the heparin-neutralizing effect, furthermore, angiogenesis inhibitory activity can be expected of PF4. Angiogenesis, which is defined as the formation of new capillaries, can be observed in healthy individuals on unusual occasions and in the ovaries or utera according to the particular stage of the menstrual cycle, and its promotion is in many instances disadvantageous to the living bodies except the process of wound healing (severe diabetic retinitis, retinopathy of prematurity, psoriasis vulgaris, malignant tumor, etc.). Especially, malignant tumor cells which are entirely free from contact inhibition need the supply of oxygen and nutrients being essential to their growth and induce angiogenesis to take place vigorously to thereby secure a route of supply for such nutrients and oxygen. Consequently, suppression of angiogenesis is considered to be effective for the suppression of malignant tumors. PF4 was reported to elicit angiogenesis inhibitory activity (Maione, T. E., et al., Science, 247, 77–79, 1990), while there was furthermore published a paper that in animal experiments, PF4 is effective for the suppression of malignant tumor cells (Shape, R. J., et al., J. Natl. Cancer Inst., 82, 848–853, 1990).

Heretofore, the purification of PF4 of a human origin has been conducted by means of heparin-immobilized affinity column chromatography using as a starting material a solution containing proteins released from platelets through stimulation of thrombin, etc. or a platelet extraction solution produced by allowing platelets to undergo hemolysis through freezing and thawing, hypotonic treatment, etc. (Levine, S. P., J. Biol. Chem., 251, 2, 324–328, 1976). However, the process has the drawbacks, such as the use of expensive heparin-immobilized affinity column and the complicated, troublesome procedures involved, and has not yet been established as an industrial process for the large-scale production of PF4 at reduced costs. Under these circumstances, the present inventors sought for a novel PF4 production process which is suited for the large-scale, mass production.

As a result, the present inventors found that a PF4-containing solution, such as a platelet extraction solution, can be contacted with a sulfated chitin to thereby allow specific adsorption and bonding of PF4 onto the sulfated chitin, and that such adsorbed PF4 can be eluted by increasing the salt concentration.

SUMMARY OF THE INVENTION

The present invention has been completed on the basis of the above finding and is concerned with a process for producing platelet factor-4, which comprises contacting a solution containing platelet factor-4 with a sulfated chitin to thereby adsorb the said factor, followed by elution of the said factor from the adsorption body.

DETAILED DESCRIPTION

As a starting material of a solution containing platelet factor-4 which is usable in the present invention, there may be mentioned, for example, platelet extraction solutions produced by allowing platelets as recovered from human blood by centrifugation to undergo freezing and thawing, hypotonic treatment or homogenization for fine pulverization, and solutions containing PF-4 which is released from platelets through stimulation with thrombin, etc.

Sulfated chitins are manufactured by sulfating a chitin produced from the outer coverings of crustaceans, and put on the market.

Sulfated chitins may have the hydroxyl groups of chitin sulfated partly or entirely and may furthermore have the acetamino groups at the 2-position partially deacetylated or sulfated.

A PF4-containing solution is desirably contacted with a sulfated chitin while keeping a pH of the solution in the neighborhood of neutrality, or about 6 to 9 in pH value, preferably about 7.5 in pH value, and a concentration of a salt in the solution desirably is less than about 1.5M, preferably about 0.4M. As a salt, there may normally be used sodium chloride and potassium chloride, and use may be made of another salts, such as sodium sulfate, unless they interfere with the adsorption of PF4.

A proportion in which a PF4-containing solution is admixed with a sulfated chitin is not particularly limited, but it is preferable to use 10 to 100 ml of a sulfated chitin against a platelet extraction solution produced from 1 liter of human blood.

A length of time for which a PF4-containing solution is contacted with a sulfated chitin is not specifically restricted, while such contacting procedure can be carried out by employing either a column method or batch method. The above contacting procedure is effected to thereby allow PF4 in the solution to be adsorbed and bonded specifically onto the sulfated chitin.

PF4 as adsorbed onto a sulfated chitin can be eluted at a pH in the neighborhood of neutrality, or about 6 to 9 in pH value, preferably about 7.5 in pH value, with use of a solution having a higher salt concentration than the one of the PF4-containing solution employed for adsorption, or not less than 0.5M, preferably not less than 1M. Preferred examples of such salt include sodium chloride, potassium chloride, etc., and simply because adsorbed PF4 is eluted by virtue of a change in ionic strength, other salts may be usable, as far as the intended object can be achieved.

PF4 as obtained in the above manner can furthermore be desalted for purification by use of Sephacryl S-100 (produced by Pharmacia of Sweden), TSK-GEL G2000 (produced by Tohsoh Inc. of Japan) and the like.

BRIEF DESCRIPTION OF THE DRAWINGS

Described in the following are the examples to illustrate the present invention in more detail, but the present invention is not understood to be limited by them, wherein in the attached drawings.

EXAMPLE 1

Production of PF4 in accordance with the present invention:

Human blood drawn was centrifuged for 6 min at 22° C. and at 3,500×g to separate out the plasma, and the remaining blood cells were admixed with a 9-fold volume of a 0.155M ammonium chloride solution and left on standing for 10 min at room temperature. Then, centrifugation was effected for 7 min. at 40° C. and at 220×g, and the white blood cells which precipitated were removed. The resultant supernatant after removal of the white blood cells was furthermore centrifuged for 10 min. at 4° C. and at 1,200×g, and the platelets which precipitated were recovered, followed by washing with isotonic saline and freezing at −20° C. The frozen platelets were thawed, admixed with a 4-fold volume of 15 mM Tris hydrochloride buffer (pH 7.6) and centrifuged for 10 min. at 4° C. and at 700×g, where the separated supernatant was made a platelet extraction solution. The platelet extraction solution was admixed with sodium chloride to the final concentration of 0.4M and added to a sulfated chitin (supplied by Fuji Spinning Co. of Japan under the tradename of Sulfonated Chitopal) equilibrated with 15 mM Tris hydrochloride/0.4M sodium chloride solution. The bonded PF4 was eluted with 15 mM Tris hydrochloride/1.0M sodium chloride solution.

In accordance with the conventional process, on the other hand, the platelet extraction solution after being admixed with sodium chloride to the final concentration of 1.0M was added, at a volume ratio of 1:1, to heparin-Sepharose (produced by Pharmacia Co. of Sweden) equilibrated with 15 mM Tris hydrochloric acid/1.0M sodium chloride solution in the same volume as that of the above-mentioned sulfated chitin, and the bonded PF4 was eluted with a 2.0M sodium chloride solution buffered with 15 mM Tris hydrochloric acid.

As a result, it was found that the process of the present invention produced 20 mg of PF4 per liter of human blood, whereas the conventional process yielded 10 mg of PF4 per liter of human blood.

Test Example 1

SDS-Polvacrylamide electrophoresis

Figure 1:
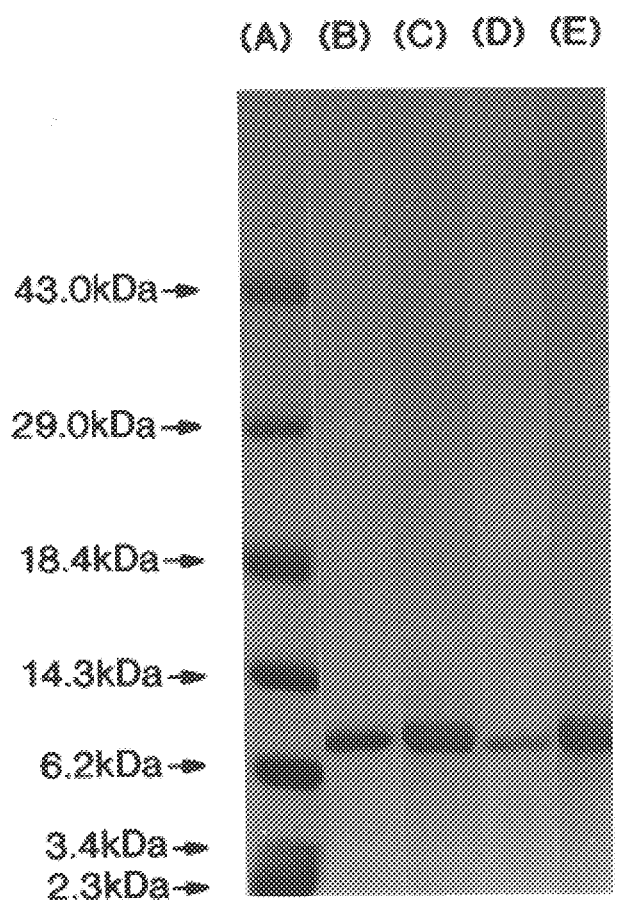
FIG. 1 is a reproduction of Western blot analysis (photograph) for platelet factors-4 produced by the process of the present invention and the conventional process.

PF4 as obtained in Example 1 and a dodecylsulfonating agent (composed of 2% SDS, 10M urea, 1 mM EDTA, 0.1M sucrose, 5% β-mercaptoethanol and 10 mM Tris-HCl, pH 7.4) were mixed in equal volumes, and the mixture was heated for 5 min. at 100° C. and then electrophoresed on a polyacrylamide gel (produced by Dai-Ichi Kagaku Yakuhin Co. of Japan with a concentration gradient of 15% to 25% in the presence of 0.1% SDS. The protein separated on the gel was stained with 0.25% Coomassie Brilliant Blue R-250 (produced by Bio-Rad Co. of USA; dissolved in 50% ethanol and 10% acetic acid), giving rise to a single band at 7.8 kDa (see FIG. 1).

Test Example 2

Western blotting method:

A protein developed on a polyacrylamide gel in the same manner as described in Example 1 was transferred electrically (conducted by supplying an electric current of 200 mA for 30 min. with use of Tris-glycine buffer containing 20% ethanol) at to a PVDF membrane (produced by Dai-Ichi Kagaku Yakuhin Co. of Japan) in a Salz Blot device (manufactured by Sartrius Co. of Germany), and the membrane was washed thoroughly with TBS (20 mM Tris and 500 mM NaCl, pH 7.5) and then held in TBS containing 50% defatted milk for 1 hour to thereby block the non-adsorbed portion. Thereafter, the membrane was reacted with a 500-fold dilution of goat's anti-human-PF4 antiserum (produced by ATAB Co. of USA) with TTBS (0.05% Tween 20, TBS) containing 1% BSA for 1 hour at room temperature, then washed thoroughly with TTBS and reacted with a 500-fold dilution of anti-goat's IgG labeled with alkaline phosphatase (produced by BioMakor Co. of USA) with TTBS containing 1% BSA. After conclusion of the reaction, coloring reaction with a substrate solution containing Nitro Blue Tetrazolium and bromochloroindolylic acid showed a single band in the same molecular weight region that in the case of SDS-polyacrylamide gel electrophoresis (see FIG. 1).

Test Example 3

Amino acid sequencing

The PF4 as obtained in Example 1 was transferred onto a PVDF membrane by the above-described procedure, followed by washing with TBS and dying with 1% acetic acid containing 0.1% Bonsoh S, and the membrane was washed successively with deionized water and methanol, and dried. The dyed portion was cut and subjected to measurement of 9 N-terminal residues with an amino-acid sequence analysis device, with the result that it was in agreement with the sequence previously reported (Duel, T. F. et al., Proc. Natl. Acad. Sci. USA, 74, 6, 2256–2258, 1977).

Test Example 4

Heparin-neutralizing activity of PF4:

Antithrombin III inhibits the activity of thrombin by binding to it, whereby such inhibition is promoted remarkably under the presence of heparin. By adding PF4 to a solution admixed with antithrombin III, thrombin and heparin, the recovered activity of thrombin was assayed and determined on the basis of the initial rate of synthetic-substrate degradation by thrombin, followed by calculation of the heparin-neutralizing activity of PF4.

Heparin (the final concentration of $7.2 \times 10^{-3}$ units/ml; produced by Wako Pure Chemicals Ind., Ltd. of Japan), PF4 as obtained in Example 1 or produced by the conventional process), antithrombin III (the final concentration of 2.9 μg/ml; produced by Seikagaku Kogyo Co. of Japan) and 40 mM HEPES (pH 7.4) were mixed to make the total volume of 2 ml, and the mixture was left on standing for 30 sec. at room temperature and admixed with 15 μl of thrombin (the final concentration of 0.18 μg/ml: produced by Sigma Co. of USA), followed by standing for 1 min at room temperature. After addition of Coloring Substrate S-2238 (the final concentration of 0.1 mM/ml: produced by Dai-Ichi Kagaku Co. of Japan), the degradation of the coloring substrate by thrombin was determined in a time-course manner by measurement of the absorbance at a wavelength of 405 nm.

Figure 2:
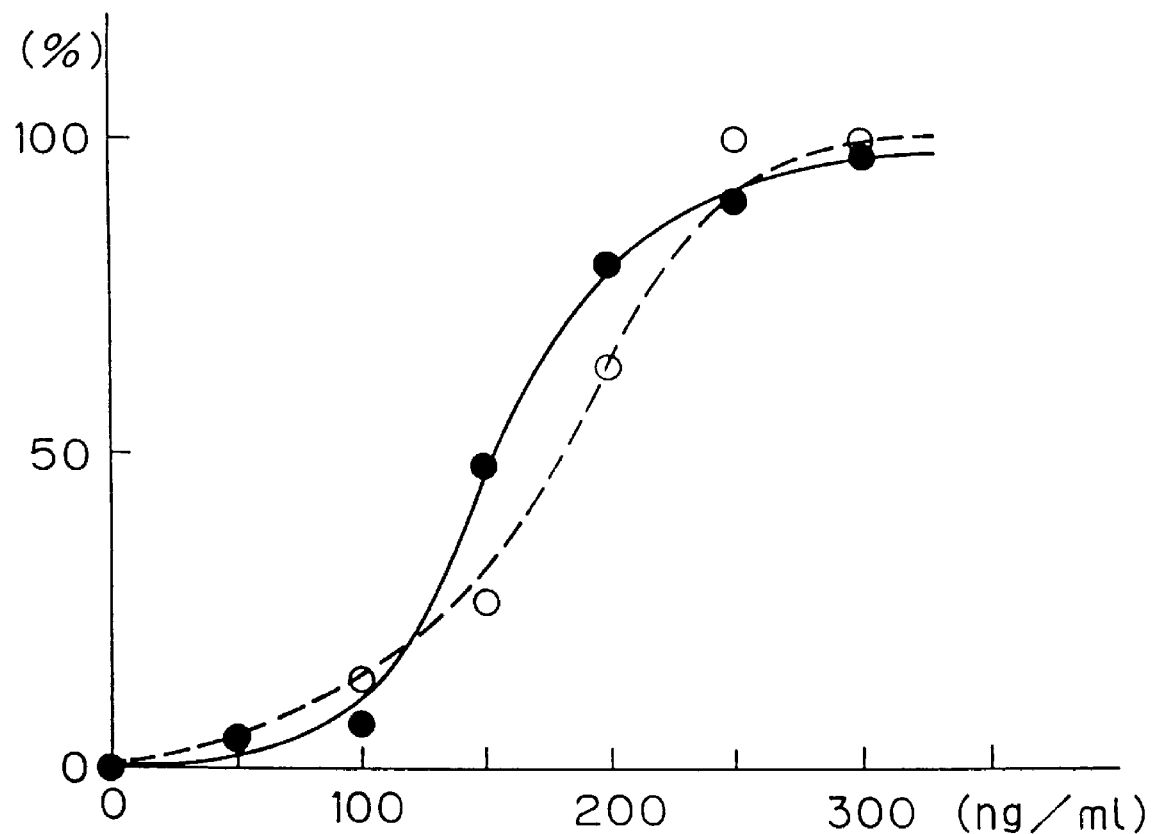
FIG. 2 is a graph illustrating the heparin-neutralizing activity of platelet factor-4 produced by the process of the present invention.

The results indicated that the PF4 as obtained in accordance with the present invention exhibited specific activity equal to that of the one produced by the conventional process (the Heparin-Sepharose method) (see FIG. 2).

We claim:

1. A process for isolating platelet factor-4, which comprises contacting a solution containing platelet factor-4 with a sulfated chitin to adsorb the said factor, followed by elution of the said factor from the adsorption body.

2. A process as claimed in claim 1, wherein a sulfated chitin is a chitin having at least part of its hydroxyl groups sulfated and its acetamino groups intact as such or partially deacetylated and sulfated.

3. A process as claimed in claim 1, wherein contact of platelet factor-4 with a sulfated chitin and elution of the said factor from the adsorption body are effected at a pH in the proximity of neutrality.

4. A process as claimed in claim 1, wherein a solution containing platelet factor-4 is incorporated with less than about 1.5M of a salt, and elution of platelet factor-4 is carried out from a sulfated chitin with a solution containing a higher concentration of a salt, with the said salt concentration being at least 0.5M.

5. A process as claimed in claim 4, wherein contact of platelet factor-4 with a sulfated chitin and elution of the said factor from the adsorption body are effected at a pH in the proximity of neutrality.

6. A process as claimed in claim 4, wherein the solution is incorporated with less than about 0.4M of a salt, and said salt concentration is at least 1M.

* * * * *